US010364459B2

(12) United States Patent
Kim et al.

(10) Patent No.: US 10,364,459 B2
(45) Date of Patent: Jul. 30, 2019

(54) METHOD OF QUANTITATIVELY AND QUALITATIVELY ANALYZING BIOMATERIAL IN REAL-TIME

(71) Applicant: SUGENTECH, Inc., Daejeon (KR)

(72) Inventors: Lee-Kyung Kim, Daejeon (KR); Mun-Cheol Paek, Daejeon (KR); Su-Jin Ku, Daejeon (KR); Sun-Young Park, Daejeon (KR); Do-Bu Lee, Incheon (KR); Jae-Hyung Park, Daejeon (KR); Ki-Chang Lee, Osan-si (KR); Nam-Joong Kim, Daejeon (KR)

(73) Assignee: SUGENTECH, Inc., Daejeon (KR)

( * ) Notice: Subject to any disclaimer, the term of this patent is extended or adjusted under 35 U.S.C. 154(b) by 805 days.

(21) Appl. No.: 14/894,985

(22) PCT Filed: May 30, 2014

(86) PCT No.: PCT/KR2014/004873
§ 371 (c)(1),
(2) Date: Mar. 14, 2016

(87) PCT Pub. No.: WO2014/193198
PCT Pub. Date: Dec. 4, 2014

(65) Prior Publication Data
US 2016/0186236 A1 Jun. 30, 2016

(30) Foreign Application Priority Data

May 30, 2013 (KR) .................. 10-2013-0061440
May 30, 2014 (KR) .................. 10-2014-0065855

(51) Int. Cl.
C12Q 1/68 (2018.01)
C12Q 1/686 (2018.01)
C12Q 1/6851 (2018.01)
C12Q 1/6818 (2018.01)
C12Q 1/6837 (2018.01)

(52) U.S. Cl.
CPC .......... C12Q 1/686 (2013.01); C12Q 1/6818 (2013.01); C12Q 1/6837 (2013.01); C12Q 1/6851 (2013.01)

(58) Field of Classification Search
CPC .. C12Q 1/6818; C12Q 1/6837; C12Q 1/6851; C12Q 2561/113; C12Q 2565/501
See application file for complete search history.

(56) References Cited

U.S. PATENT DOCUMENTS

2010/0015626 A1   1/2010  Oliphant et al.
2013/0303390 A1*  11/2013 Seo .................. B01L 3/50853
                                                        506/9

FOREIGN PATENT DOCUMENTS

| CN | 102382900 A    | 3/2012 |
| EP | 2662452 A1     | 7/2012 |
| KR | 1020100102560 A | 9/2010 |
| KR | 101168166 B1   | 7/2012 |
| KR | 101184566 B1   | 9/2012 |
| KR | 1020130101952 A | 9/2013 |
| WO | 2008094273 A2  | 8/2008 |
| WO | 2012/051504 A2 | 4/2012 |
| WO | 2012/096430 A1 | 7/2012 |

OTHER PUBLICATIONS

Database search results, reference No. XP-002756765, dated Mar. 21, 2012 for "Real-time fluorescence quantitative polymerase chain reaction detection for porcine circovirus 2, includes designing and synthesizing specific upstream primer, downstream primer and probe", corresponding to foreign patent document CN102382900A, 1 page.
Extended European Search Report dated May 20, 2016 in connection with the counterpart European Patent Application No. 14804620. 4-1404.
International Search Report for PCT/KR2014/004873 dated Sep. 26, 2014.

* cited by examiner

Primary Examiner — David C Thomas
(74) Attorney, Agent, or Firm — Hauptman Ham, LLP

(57) ABSTRACT

A method of quantitatively and qualitatively analyzing a biomaterial in real-time, the method comprising preparing a device for detecting a biomaterial, feeding a complex of first and second probes, a forward primer, a reverse primer, a sample comprising deoxynucleotide triphosphate, a polymerase having exonuclease activity, and a sample comprising target genes, and a reaction solution comprising a buffer into the reaction container, performing polymerase chain reaction comprising denaturation of the target genes in the sample, hybridization of the target genes, the complex, and the forward and reverse primers in the sample, and elongation of the primers through the polymerase having exonuclease activity, allowing for elongation of the second probe on the third probe by the polymerase after hybridizing the released second probe and the third probe fixed to the biochip, detecting a first fluorescence signal by the first phosphor and a second fluorescence signal by the second phosphor.

17 Claims, 11 Drawing Sheets

METHOD OF QUANTITATIVELY AND QUALITATIVELY ANALYZING BIOMATERIAL IN REAL-TIME

TECHNICAL FIELD

The present invention relates to a method of quantitatively and qualitatively analyzing a biomaterial in real-time. More particularly, the present invention relates to a method of quantitatively and qualitatively analyzing a biomaterial in real-time by integrally performing real-time Polymerase Chain Reaction (PCR) and DNA microarray in the same space.

BACKGROUND ART

Methods which are currently, generally used in molecular diagnostics to detect target genes of analytes are broadly classified into quantitative methods and qualitative methods.

A quantitative method is a method of relatively or absolutely measuring expression levels and copy numbers of target genes. On the other hand, a qualitative method is a method of analyzing existence and genotypes of target genes.

As a quantitative detection method, there is real-time Polymerase Chain Reaction (real-time PCR). A detection method using real-time PCR is broadly used due to advantages thereof wherein quantitative analysis is possible, and sample contamination risk by air can be reduced because gene amplification signals from the samples can be obtained, without opening a tube containing the samples, after mixing with a reagent. However, since a number of fluorescences simultaneously detectable in one tube is up to six, several tubes are necessary in fields in which dozens of gene mutations and genotypes are examined.

As a large-scale qualitative detection method, there is a method using a DNA microarray. This method using a DNA microarray has an advantage in that multiple target probes are fixed to a surface and thus a variety of genes can be detected at one time using one phosphor. However, there is a limitation that quantitative analysis is impossible.

Recently, research into a quantitative and qualitative detection method to address drawbacks of such a qualitative or quantitative detection method is underway. As a result of such research, technology enabling quantitative analysis to be performed in one container using real-time PCR, and multianalysis to be possible by reacting amplified genes with probes fixed to a solid bottom of a container was developed. However, this technology has a limitation that, in order to obtain probe signals, the probe signals should be read by means of a separate scanner, after opening or washing a container.

Korean Patent Laid-Open Publication No. 2010-0102560 as a related technology, published on Sep. 24, 2010, discloses a method of detecting nucleic acids using an integrated device for real-time nucleic acid analysis and a method of detecting target nucleic acids using the same.

DISCLOSURE

Technical Problem

Therefore, the present invention has been made in view of the above problems, and an object of the present invention is to provide a method simultaneously performing quantitative and qualitative analyses of reacted products in a single reaction container, using a biochip to which probes for quantitatively and qualitatively analyzing reacted products amplified through real-time polymerase chain reaction (real-time PCR) and distinguishing target genes are fixed.

Technical Solution

In accordance with one aspect of the present invention, provided is a method of quantitatively and qualitatively analyzing a biomaterial in real-time, the method including: preparing a device for detecting a biomaterial, wherein the device includes a reaction container including an opening at an upper part thereof; and an element part separatively connected to the reaction container via the opening, wherein the element part includes a cap coupled to the opening of the reaction container; and a rod extended from a lower part of the cap, wherein the rod includes a biochip having a third probe fixed to a surface of the biochip; feeding a complex of first and second probes, a forward primer, a reverse primer, a sample including deoxynucleotide triphosphate (dNTP), a polymerase having exonuclease activity, and a sample including target genes, and a reaction solution including a buffer into the reaction container, wherein the first probe includes oligonucleotide sequences complementary to nucleic acid sequences of the target genes in the sample, a first phosphor for generating a first fluorescence signal, and a first quencher for quenching the first phosphor, the second probe does not include oligonucleotide sequences complementary to the nucleic acid sequences of the target genes in the sample, but includes oligonucleotide sequences complementary to the third probe, and the forward and reverse primers include oligonucleotide sequences complementary to the nucleic acid sequences of the target genes to amplify the target genes in the sample; performing polymerase chain reaction including denaturation of the target genes in the sample, hybridization of the target genes, the complex, and the forward and reverse primers in the sample, and elongation of the primers through the polymerase having exonuclease activity, wherein the hybridization is only performed between the target genes and the first probe of the complex, and the second probe and the first phosphor are disassembled and released from the complex during elongation by the polymerase having exonuclease activity; allowing elongation of the second probe on the third probe by the polymerase after hybridizing the released second probe and the third probe fixed to the biochip, wherein the third probe includes a second phosphor for generating a second fluorescence signal and a second quencher for quenching the second phosphor, and the second quencher is spaced from the second phosphor according to elongation of the second probe on the third probe to emit light; and detecting a first fluorescence signal by the first phosphor and a second fluorescence signal by the second phosphor.

Advantageous Effects

In accordance with a method of quantitatively and qualitatively analyzing a biomaterial in real-time according to an embodiment of the present invention, inconvenience and low economic feasibility of conventional technologies requiring several to dozens of reaction containers (tubes) depending upon gene types can be addressed In addition, the present invention enables quantitative and qualitative analyses to be simultaneously performed by integrally performing real-time PCR and DNA microarray in real-time in a single reaction container. This method also addresses disadvantages of DNA microarrays, which have difficulty in application to quantitative analysis.

In particular, the method of quantitatively and qualitatively analyzing a biomaterial in real-time according to the present invention enables the quantitative and qualitative analyses to be possible without opening or washing the container by obtaining signals of a DNA chip in a reaction container in real-time, and quantitative analysis and genetype examination to be economically, reliably carried out at the same time in a variety of molecular diagnosis fields such as drug resistance examination, somatic mutation examination, and single nucleotide polymorphism examination as well as infectious disease examination.

Therefore, the method of quantitatively and qualitatively analyzing a biomaterial in real-time according to the present invention can be easily used in all molecular diagnosis fields regardless of analysis type, gene type, or examination type.

DESCRIPTION OF DRAWINGS

FIG. 11 illustrates a trans-type fluorescence signal detection method, FIG. 12 illustrates an oblique-type fluorescence signal detection method, and FIG. 13 illustrates an epi-type fluorescence signal detection method.

BEST MODE

Figure 1:
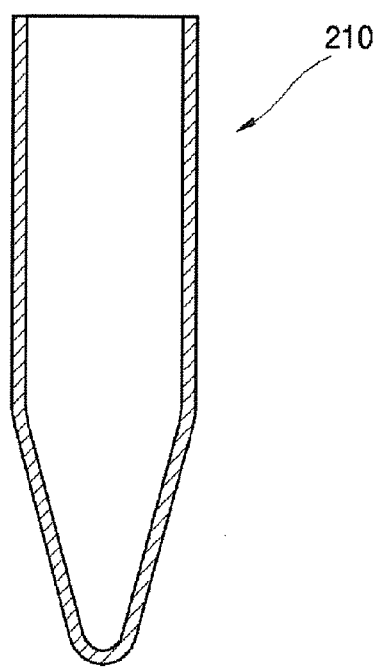
FIG. 1 schematically illustrates a reaction container of a biomaterial detection device according to an embodiment of the present invention.

In order to aid in understanding of the present invention, specific terms are defined in the present invention. Unless otherwise defined, scientific and technical terms and technical used in the present invention will have meanings that are generally understood by those skilled in the art. In addition, it will be understood that singular forms "a" "an" and "the" are intended to encompass the plural forms as well, unless the context clearly indicates otherwise, and plural terms encompass singular forms thereof.

In addition, each step of methods disclosed in the present invention is not intended to be accurately carried out in disclosed sequences unless otherwise mentioned and may be variously modified and changed within a range of a technical spirit in which purposes of the present invention are accomplished.

Hereinafter, a method of quantitatively and qualitatively analyzing a biomaterial according to an embodiment of the present invention is described in detail.

According to an embodiment of the present invention, a method of quantitatively and qualitatively analyzing a biomaterial in real-time is provided. The method includes (a) preparing a device for detecting a biomaterial, wherein the device includes a reaction container including an opening at an upper part thereof; and an element part separatably connected to the reaction container via the opening, wherein the element part includes a cap coupled to the opening of the reaction container; and a rod extended from a lower part of the cap, wherein the rod includes a biochip having a third probe fixed to a surface of the biochip; (b) feeding a complex of first and second probes, a forward primer, a reverse primer, a sample including deoxynucleotide triphosphate (dNTP), a polymerase having exonuclease activity, and a sample including target genes, and a reaction solution including a buffer into the reaction container, wherein the first probe includes oligonucleotide sequences complementary to nucleic acid sequences of the target genes in the sample, a first phosphor for generating a first fluorescence signal, and a first quencher for quenching the first phosphor, the second probe does not include oligonucleotide sequences complementary to the nucleic acid sequences of the target genes in the sample, but includes oligonucleotide sequences complementary to the third probe, and the forward and reverse primers include oligonucleotide sequences complementary to the nucleic acid sequences of the target genes to amplify the target genes in the sample; (c) performing polymerase chain reaction including denaturation of the target genes in the sample, hybridization of the target genes, the complex, and the forward and reverse primers in the sample, and elongation of the primers through the polymerase having exonuclease activity, wherein the hybridization is only performed between the target genes and the first probe of the complex, and the second probe and the first phosphor are disassembled and released from the complex during elongation by the polymerase having exonuclease activity; (d) allowing elongation of the second probe on the third probe by the polymerase after hybridizing the released second probe and the third probe fixed to the biochip, wherein the third probe includes a second phosphor for generating a second fluorescence signal and a second quencher for quenching the second phosphor, and the second quencher is spaced from the second phosphor according to elongation of the second probe on the third probe to emit light; and (e) detecting a first fluorescence signal by the first phosphor and a second fluorescence signal by the second phosphor.

First, a step (a) of preparing a device for detecting a biomaterial used in the method of quantitatively and qualitatively analyzing a biomaterial in real-time is disclosed.

Figure 2:
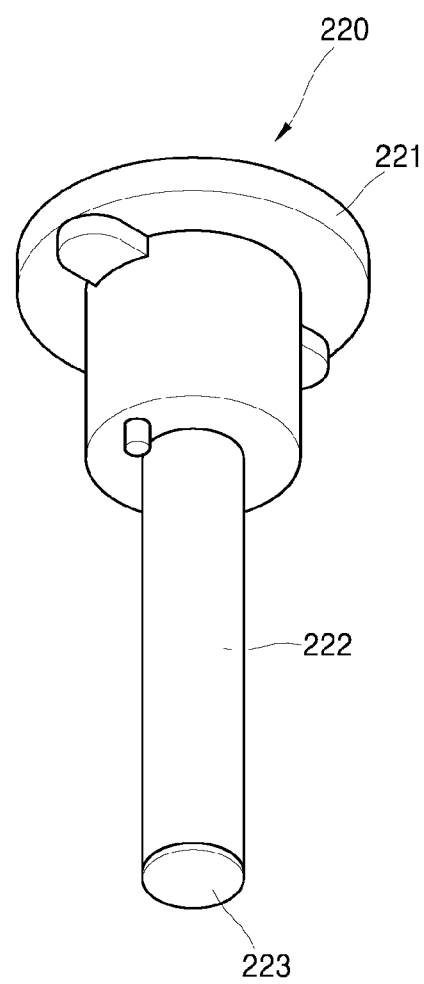
FIG. 2 schematically illustrates an element part of a biomaterial detection device according to an embodiment of the present invention.
Figure 3:
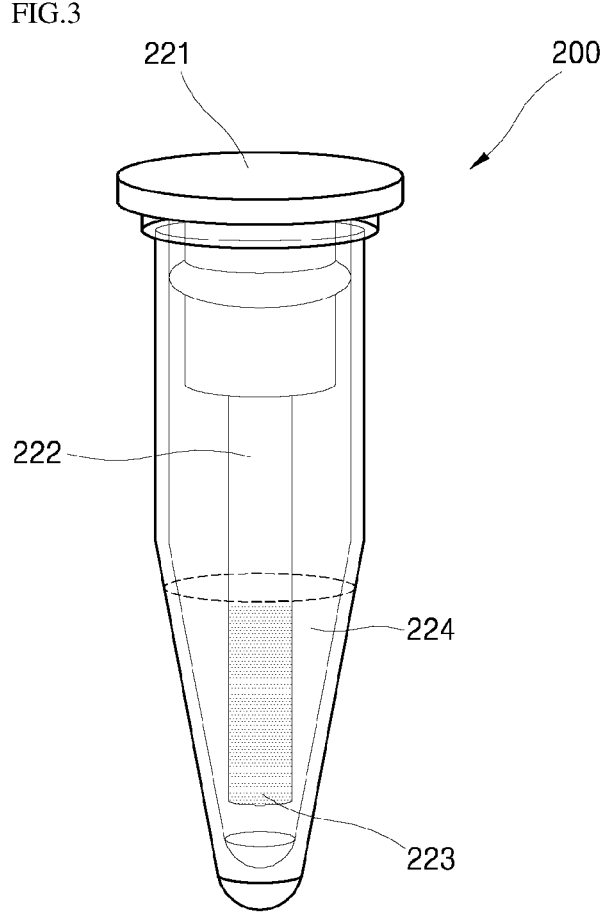
FIG. 3 illustrates a biomaterial detection device including the reaction container and the element part, which are coupled, according to an embodiment of the present invention.
Figure 4:
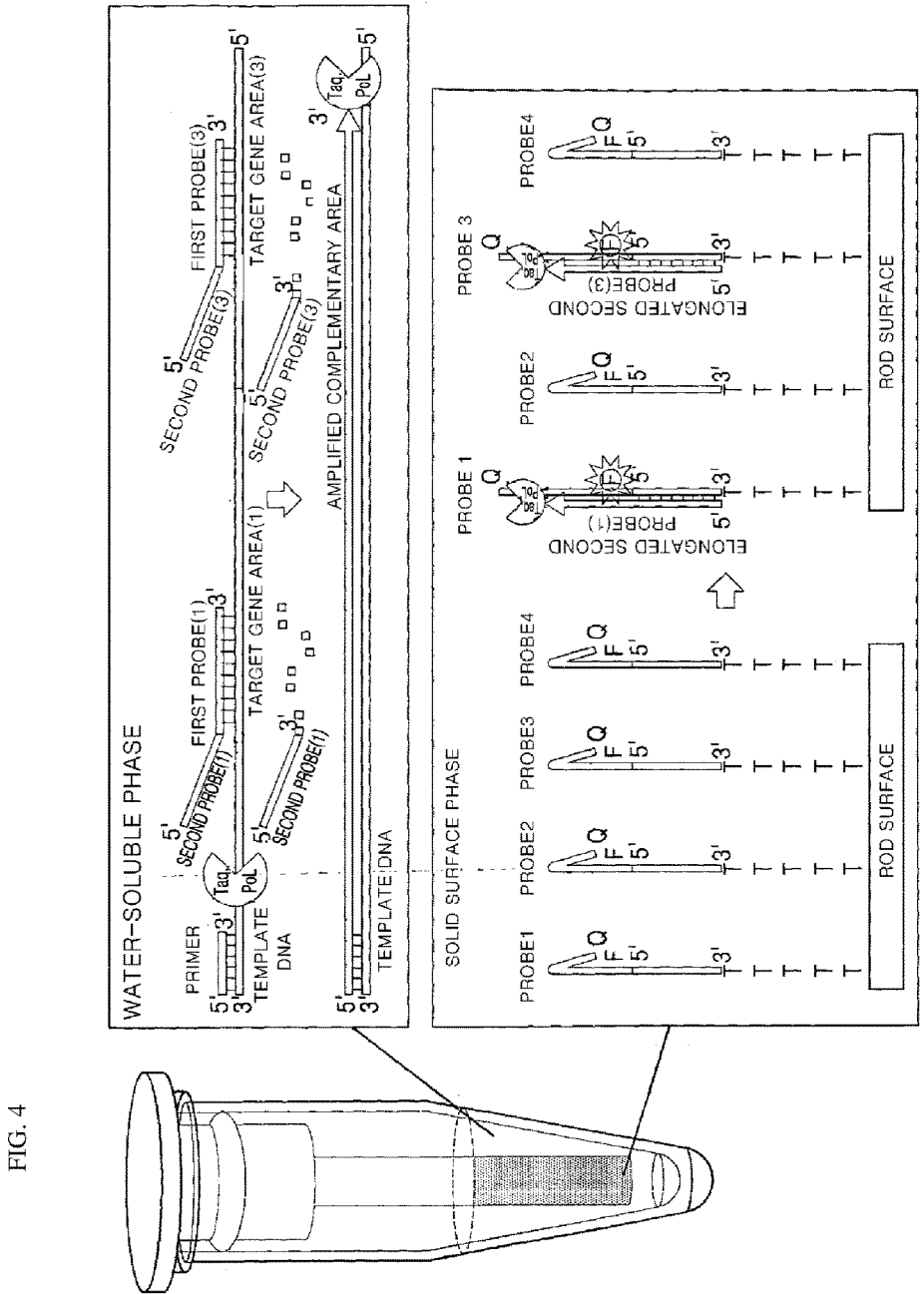
FIG. 4 schematically illustrates reaction in a biomaterial detection device according to an embodiment of the present invention.

Referring to FIGS. 1 to 3, the device for detecting a biomaterial 200 includes a reaction container 210 including an opening at an upper part thereof and a element part 220 separatably connected to the reaction container 210 via the opening. Here, the element part 220 includes a cap 221 coupled with an opening of the reaction container 210 and the rod 222 extended from a lower part of the cap 221. The rod includes a biochip 223 having a third probe fixed to a surface of the biochip.

Here, the rod 222 is extended from the lower part in a length in which the biochip 223 provided at a surface of the rod 222 is submerged in the reaction solution when the reaction solution 240 is fed into the reaction container 210 in the subsequent step b.

The biochip 223 may be provided at at least one area selected from an outer peripheral surface and a lower part of the rod 222. Here, the at least one area at which the biochip 223 is provided is present in a location in which the reaction solution may be submerged.

In an embodiment, the cap 221 may be formed of a material having a light transmittance of 50% or more. In this case, a fluorescence signal may be detected in an upper direction of the cap 221 without opening of the cap 221 as in a trans-type fluorescence signal detection method. More particularly, the cap 221 may be made of a material selected from glass, quartz, fumed silica, acryl, polycarbonate, cycloolefin copolymer (COC) and cycloolefin polymer (COP).

In another embodiment, when a fluorescence signal is not detected in an upper direction of the cap 221 as in an oblique-type fluorescence signal detection method or an epi-type fluorescence signal detection method, it is not essential that a light transmittance of the cap 221 is 50% or more.

In another embodiment, the rod 222 may be made of a material having a low thermal expansion coefficient of $9.0 \times 10^{-6}$/m·K or less. When the thermal expansion coefficient of the rod 222 is greater than $9.0 \times 10^{-6}$/m·K, durability of the element part is overall decreased and trouble may occur. Preferably, the rod 222 may be made of a material having a thermal expansion coefficient of $5.5 \times 10^{-7}$/m·K to $9.0 \times 10^{-6}$/m·K, when it is considered that exact fluorescence detection becomes difficult due to a difference from the thermal expansion coefficients of other materials according to temperature change when the thermal expansion coefficient of the rod is excessively low. As unlimited examples of a material having such a thermal expansion coefficient, there is at least one polymer selected from quartz, fumed silica, COC, and COP.

In an embodiment, the rod 222 includes the biochip 223, the third probe is fixed to a surface of which. Here, the third probe may be directly or indirectly fixed to the biochip 223 via a 5' or 3' terminal polymer material. Preferably, the 5' terminal or 3' terminal polymer material of the third probe may be a poly-T tail or a ploy A-tail. In addition, the terminal of the polymer material, i.e., a part fixed to the biochip 223 may be modified to a specific functional group depending upon characteristics of the biochip 223.

For example, when the biochip 223 is composed of an aldehyde (CHO) coating substrate, an isothiocyanate (NCS) coating substrate, an epoxide coating substrate, a carboxylated substrate, or a phosphorylated substrate, the poly-T tail or poly A-tail terminal, i.e., a part fixed to the biochip 223, of the third probe is aminated to be fixed to the substrate. On the other hand, when the biochip 223 is composed of an aminated substrate, the poly-T tail or poly A-tail의 terminal, i.e., a part fixed to the biochip 223, of the third probe is carboxylated or phosphorylated to be fixed to the substrate.

As described above, in a method according to an embodiment of the present invention, step (a) aims to provide the device for detecting a biomaterial 200 such that quantitative and qualitative analyses may be simultaneously carried out by performing integrally real-time PCR and DNA microarray in real-time in a single reaction container.

When the device for detecting a biomaterial 200 is used, real-time PCR and DNA microarray may be integrally carried out in real-time in a state in which the element part 220 is coupled with the reaction container 210, i.e., the device for detecting a biomaterial 200 is not opened. In addition, since the device for detecting a biomaterial 200 is present in a state in which it coupled with the reaction container 210, i.e., in a state in which the device for detecting a biomaterial 200 is not opened, when real-time PCR and DNA microarray are carried out in repeated cycles, the device for detecting a biomaterial 200 may be blocked from outside contaminants and thus is not needed to be repeatedly washed.

Subsequently, step (b) of feeding a reaction solution into the reaction container 210 is disclosed. In this step (b), the reaction solution is fed such that the biochip 223 provided at the rod 222, more particularly the third probe fixed (or adhering) to the biochip 223, is sufficiently submerged in the reaction solution.

In addition, when biochips 223 are provided at at least one area selected from the outer peripheral surface and the lower part of the rod 222, the reaction solution is added such that all third probes fixed (or adhering) to the at least one area at which the biochips 223 are provided, more particularly the biochips 223 provided at the at least one area, are sufficiently submerged in the reaction solution. Here, real-time PCR is carried out in the reaction solution (water-soluble phase), and DNA microarray is carried out at a third probe (on solid surface) fixed to the biochip 223.

The reaction solution includes a complex of first and second probes, a forward primer, a reverse primer, deoxynucleotide triphosphate (dNTP), a polymerase having exonuclease activity, a sample including target genes, and a buffer.

The first probe includes oligonucleotide sequences complementary to nucleic acid sequences of the target genes in the sample, a first phosphor generating a first fluorescence signal, and a first quencher for quenching the first phosphor.

The second probe does not include oligonucleotide sequences complementary to nucleic acid sequences of the target genes in the sample and includes oligonucleotide sequences complementary to the third probe.

Here, the lengths of the first and second probes are not specifically limited so long as each thereof forms proper dimers with the target genes and the third probe. For example, the sizes of the probes may be 15 mer to 50 mer, but the present invention is not limited thereto.

In addition, when the first and second probes have the same or different target genes as targets, they may be composed of probes including different oligonucleotide sequences. That is, different complexes composed of the first and second probes targeting a single area or plurality of target areas of a target gene, or a single area or a plurality of areas of a plurality of target genes may be used.

For example, a first probe X may form a complex with a second probe X, and a first probe Y may form a complex with a second probe Y. Here, the first probe X may hybridize with complementary target areas X of the target genes, and the first probe Y may hybridize with complementary target areas Y of the target genes. In addition, a first phosphor X included in the first probe X and a first phosphor Y included in the first probe Y may include a fluorescent material generating fluorescence signals detected in different wavelength ranges.

Additionally, third probes may be used. That is, a third probe X may hybridize with the second probe X, and the third probe Y may hybridize with the second probe Y.

The expression "probe" used in the present invention indicates a natural or modified monomer or linear oligomers having coupling including deoxyribonucleotides and ribonucleotides hybridizable with specific nucleotide sequences.

The probe is preferably a single strand to exhibit maximum efficiency during hybridization. The probe is preferably deoxyribonucleotide.

The expression "nucleotide" or "polynucleotide" in the present invention indicates deoxyribonucleotide or ribonucleotide which is present in a single or double strand form, and includes forms similar to the nucleotide unless otherwise mentioned.

Here, the first and second probes in the reaction solution are present in a complex state. In the complex, the first and second probes may be directly connected to each other, or the first probe may be connected to the second probe via a suitable linker.

The forward and reverse primers include oligonucleotide sequences complementary to the nucleic acid sequences of the target genes to amplify the target genes in the sample.

The expression "primer" used in the present specification indicates an oligonucleotide, and may be function as a start site for synthesis under a condition in which synthesis of a product elongated by complementary primers is induced on a nucleic acid chain (template), i.e., under a condition in which a nucleotide and such a polymerization agent as a DNA polymerase are present and temperature and pH are suitable. Preferably, the primer is deoxyribonucleotide and a single chain.

The forward and reverse primers (a pair of primers) should have a sufficiently long length such that synthesis of an elongated product is primed in the presence of a polymerase. Although suitable lengths of the primers are dependent upon multiple factors, e.g., temperature, application fields, and sources of the primers, they may be properly selected within a range of 15 mer to 50 mer.

A pair of the primers includes target-specific sequences (oligonucleotide sequences hybridized with a target). Here, the expression "target-specific sequences" means sequences complementary to nucleic acid sequences of the target genes in the sample. The target-specific sequences locate in a 3' direction within a location of the pair of the primers.

The expression "complementary" used in the present invention means complementarity allowing selective hybridization with the nucleotide sequences under any specific hybridization or annealing condition, includes the expressions "substantially complementary" and "perfectly complementary", and, preferably, means the expression "perfectly complementary".

Figure 5:
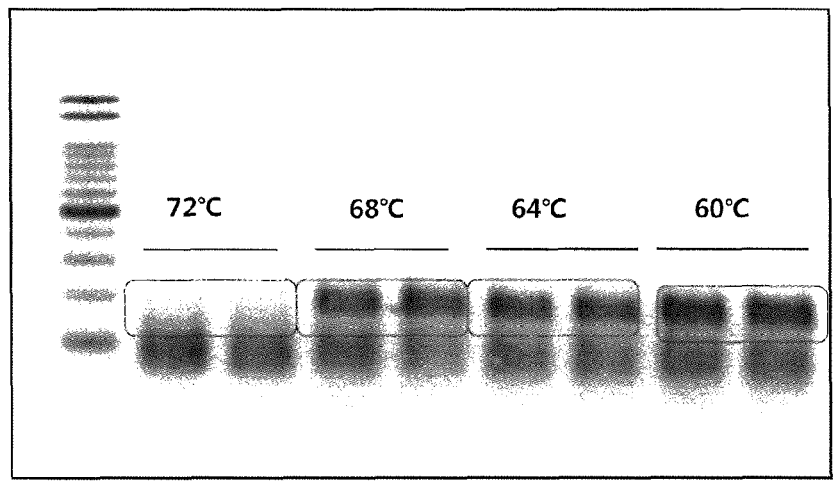
FIG. 5 illustrates activation temperatures of a polymerase used in an embodiment of the present invention.

The polymerase having exonuclease activity is a thermally stable polymerase having preferably 5' exonuclease activity, more preferably 5' exonuclease activity. Here, the expression "thermally stable" means that the polymerase is stable without denaturation under a high-temperature polymerization condition, more particularly that stability of the polymerase may be maintained at 50° C. to 65° C. Therefore, the thermally stable polymerase is activated at 50° C. to 65° C. (see FIG. 5).

The thermally stable polymerase may be isolated from bacteria from which the thermally stable (DNA) polymerase may be obtained. Examples of the bacteria include *Thermus aquaticus* (Taq), *Thermus thermophilus* (Tth), *Thermus filiformis, Thermis flavus, Thermococcus literalis, Pyrococcus furiosus* (Pfu), and the like. More preferably, the polymerase having exonuclease activity is a thermally stable Taq polymerase having 5' exonuclease activity.

Examples of the sample include solutions, body fluids, blood, cells, tissues, and organs including target genes, but the present is not limited thereto.

The polymerase having exonuclease activity in the reaction solution may be used in an amount of 0.1 unit to 1 unit per reaction, and the complex of the first and second probes in the reaction solution may be used in an amount of 0.5 pmoles to 10 pmoles per reaction. As a use amount of each of the polymerase and the complex is gradually increased, reactivity thereof represents a Gaussian-type graph, and, within the ranges, reactivity of real-time PCR may be maximally maintained.

In addition, the forward and reverse primers in the reaction solution may be used in a symmetric or asymmetric concentration.

Subsequently, a real-time PCR step (step (c)) to amplify the target genes in the sample is disclosed. The real-time PCR step includes denaturation of the target genes in the sample, hybridization of the target genes, the complex, and the forward and reverse primers in the sample, and a polymerase chain reaction including elongation of the primers through the polymerase having exonuclease activity.

Here, one cycle is that the denaturation reaction, hybridization reaction and elongation reaction is sequentially carried out once. In the real-time PCR, the denaturation reaction, the hybridization reaction and the elongation reaction may be sequentially in several times (n) (n cycles).

Real-time PCR according to the step (c) is carried out in the reaction solution in the device for detecting a biomaterial 200.

First, the denaturation reaction for the target genes in the sample allows that each single-strand template DNA functions as a template of the forward and reverse primers by separating double-stranded template DNAs of the target genes to a single strand form. The denaturation reaction may be carried out at 92° C. to 98° C.

After double-stranded template DNAs are denatured into single-strand template DNAs, the forward and reverse primers are respectively hybridized (or annealed) with each single strand template DNA, and the first and second probes are also hybridized with one area of single-strand template DNAs.

The expression "hybridization" used in the present invention indicates that two single-strand nucleic acids form duplex structures pair through paring of complementary base sequences. The hybridization may occur when complementarity between single-stand nucleic acid sequences is perfect or where are several mismatched bases. Complementarity for hybridization may be dependent upon a hybridization reaction condition and controlled by particular temperature.

Here, in the target genes and the complex, the hybridization reaction is only carried out between the first probe and the target genes, and the second probe is coupled with the first probe, but does not hybridize with the target genes.

Subsequently, the primers are elongated by the polymerase having exonuclease activity. Here, during elongation reaction by the polymerase having exonuclease activity, when the polymerase reaches the complex hybridized with the target genes, the polymerase performs elongation reaction through its own activity while disassembling the complex. Here, the second probe and the first phosphor are disassembled from the complex and released into the reaction solution.

Before the disassembling, the first phosphor in the complex is quenched by the first quencher. However, when the first phosphor is released according to disassembling of the complex by the polymerase, the first phosphor is deviated from a quenched state and a first fluorescence signal occurs within a corresponding wavelength range.

Accordingly, when target genes having sequences complementary to the first probe are not present in the sample, the second probe and the first phosphor are not disassembled and are not present in the reaction solution. In addition, when target genes having sequences complementary to the first probe are not present in the sample, the first phosphor is quenched by the first quencher and thus a first fluorescence signal by the first phosphor is not generated.

On the other hand, when target genes having sequences complementary to the first probe are present in the sample, the first probe of the complex of the first and second probes and the forward and reverse primers are hybridized to complementary sites of the target genes after denaturation of double-stranded template DNAs of the target genes, and the second probe is bonded to the first probe, but is not hybridized with the target genes.

Subsequently, the elongation is carried out by a polymerase having 5' exonuclease activity at an elongation temperature of the primers, and during the elongation of the primers, the second probe and the first phosphor are disassembled by the polymerase and released from the complex hybridized at complementary sites of the target genes.

Figure 6:
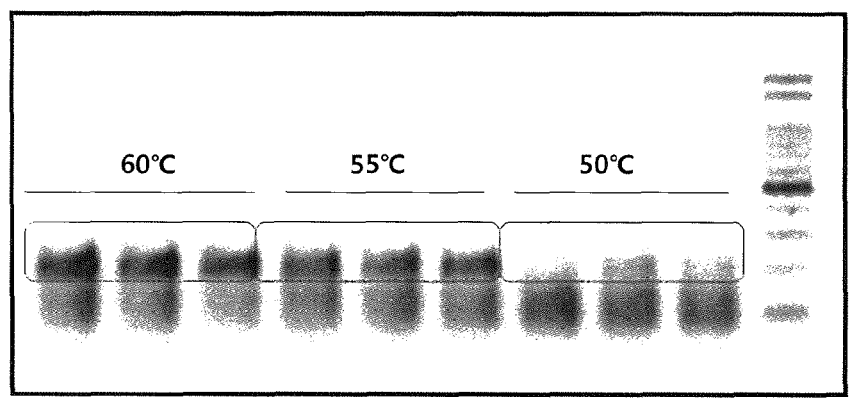
FIG. 6 illustrates elongation temperature conditions of real-time PCR carried out in an embodiment of the present invention.

Here, the elongation of the primers by the polymerase may be carried out at 50° C. to 70° C., preferably 55° C. to 68° C., more preferably 60° C. The elongation temperature of the primer is directly related to elongation efficiency of the primer (see FIG. 6).

When target genes having sequences complementary to the first probe are no present in the sample, or when target genes having sequences complementary to the first probe are present in the sample but the complex is not hybridized at complementary sites of the target, the complex is not disassembled by the polymerase having 5' exonuclease activity. Accordingly, the second probe and the first phosphor are not disassembled and are not released into the reaction solution. That is, when hybridization of the target genes and the complex is carried out, the second probe and the first phosphor may freely present in the reaction solution.

Accordingly, when target genes having sequences complementary to the first probe are present in the sample, the target genes are gradually amplified according to a repeated frequency (cycle) of the real-time PCR according to the step (c), and the amounts of the second probe and the first phosphor freely present in the reaction solution also increase in conjunction with amplification of the target genes.

An increased amount of the first phosphor in the reaction solution increases the intensity of the first fluorescence signal.

Next, DNA microarray on the biochip 223 (step (d)) is initiated using the second probe released into the reaction solution through the real-time PCR reaction.

As described above, the third probe is fixed onto a surface of the biochip 223. Here, the third probe includes the second phosphor for generating the second fluorescence signal and the second quencher for quenching the second phosphor. Here, the second phosphor and the second quencher included in the third probe are disposed closely to each other, and thus, may be present as a secondary structure (e.g., in a loop or hairpin form) in which the second phosphor may be quenched by the second quencher (molecular beacon).

Here, when different complexes composed of the first and second probes which target a plurality of target areas of the target genes are used as described above and target genes having sequences complementary to the first probes X and Y are present in the sample, the second probes X and Y are disassembled from the plurality of the complex and released into the reaction solution as a result of the real-time PCR according to the step (c), and the second probes X and Y may be hybridized with the plurality of the third probes, i.e., the third probe X and the third probe Y.

In the step (d), the second probe released at step (c) and the third probe fixed to the biochip are hybridized, and then, the second probe is elongated on the third probe by the polymerase. When the second probe is elongated on the third probe, the secondary structure of the third probe is disassembled, and thus, the second phosphor is released from a quenched state that is formed by the second quencher.

In order to describe step (d) in more detail, a relation between the step (c) and the step (d) is described. The real-time PCR according to step (c) and the DNA microarray according to step (d) may be sequentially or independently carried out in repeated cycles in a single (identical) device for detecting a biomaterial 200. In other words, it is not essential to sequentially perform step (c) and step (d).

That is, the second probe is disassembled from the complex through step (c) at a first cycle and released into the reaction solution. Subsequently, the second probe is hybridized with the third probe fixed to the biochip 223 at temperature for hybridization reaction of step (C) at a second cycle.

In a state in which a first cycle of real-time PCR is completed and thus the second probe is released into the reaction solution, a second cycle of the real-time PCR is initiated, and a secondary structure of the third probe is unwound at temperature at which denaturation reaction (denaturation of double-stranded template DNAs of the target genes) of the second cycle is carried out. That is, at temperature at which the denaturation reaction of the second cycle is carried out, the second phosphor included in the third probe is present in a state in which the second phosphor is not quenched by the second quencher.

Subsequently, the second probe is hybridized with a complementary area of the third probe at temperature at which a hybridization reaction of the second cycle of the real-time PCR is carried out, and the second probe is elongated on the third probe at temperature at which an elongation reaction is carried out by the polymerase. Accordingly, the secondary structure of the third probe may be maintained in an unwound state.

As described above, the second probe is hybridized with the third probe and then elongation is carried out at temperature at which step (c) is carried out, and thus, all secondary structures are present in an unwound state regardless of whether the secondary structure of the third probe is maintained in an unwound state. Therefore, the second phosphor included in the third probe is present in a state in which the second phosphor is not quenched by the second quencher.

Therefore, after step (d), lowering temperature such that the secondary structure of the third probe is recovered may be further included. In this step, a secondary structure of a third probe with which the second probe is hybridized and thus which is not elongated is recovered, and thus, the second phosphor may be quenched by the second quencher again. That is, this additional step is a step of quenching the second phosphor, and thus, non-specific second fluorescence signal of the second phosphor, which occurs when the second probe is not elongated on the third probe, may be excluded.

Figure 7:
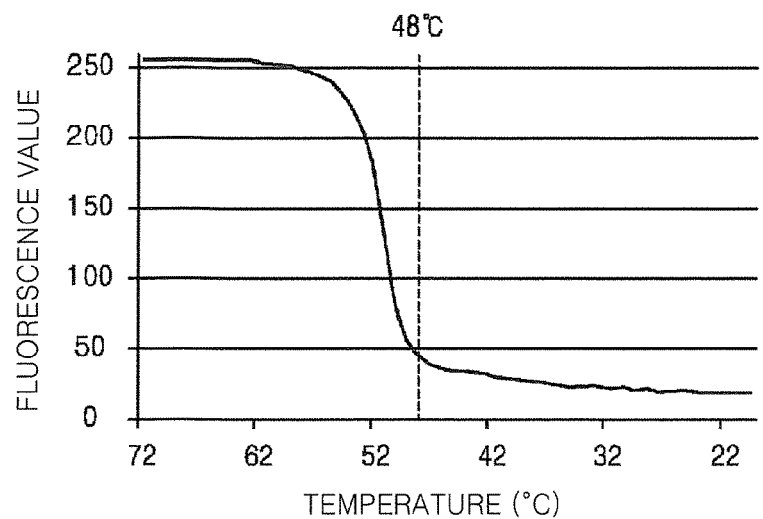
FIG. 7 illustrates change in a second fluorescence signal depending upon temperature change in a third element part according to an embodiment of the present invention.

Here, temperature at which the secondary structure of the third probe may be recovered is 50° C. or less (see FIG. 7). That is, the secondary structure of the third probe is preferred to be designed such that the secondary structure may be recovered at 50° C. or less. More particularly, the third probe includes the second phosphor and the second quencher. Here, the second phosphor is present as a secondary structure to be quenched by the second quencher closely locating thereat, and the third probe is present as a secondary structure to be present in an unwound state at temperature at which denaturation of the double-stranded template DNAs of the target genes is carried out. In addition, the third probe is present in a state in which the secondary structure thereof may be recovered again at 50° C. or less, when the third probe present in a state in which a secondary structure thereof is unwound is hybridized by the second probe and thus is not elongated.

The third probe may recover an original secondary structure thereof according to temperature decrease in a state in which the third probe is not elongated due to hybridization of the second probe. The second fluorescence signal starts to be decreased at 56° C. or less, preferably 50° C. or less. More preferably, the second fluorescence signal may be completely quenched at 48° C. or less.

Figure 8:
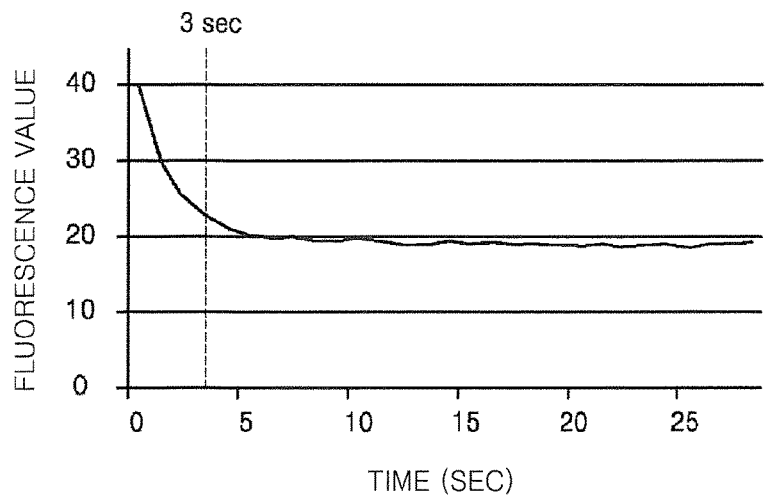
FIG. 8 illustrates change in a second fluorescence signal depending upon time change in a third element part according to an embodiment of the present invention.

In addition, time at which the secondary structure of the third probe may be recovered may be five seconds or more within the temperature range (see FIG. 8). The third probe in a state in which the second probe is hybridized therewith and thus elongation thereof is not carried out gradually losses a second fluorescence signal thereof when temperature is maintained at 50° C. or less. Here, the temperature is maintained for 3 seconds or more, preferably five seconds or more.

When the second probe is not freely present in the reaction solution According to the additional step of quenching the third probe, the second fluorescence signal by the second phosphor, derived from the third probe is not generated.

Finally, step (e) of detecting the first and second fluorescence signals generated from the device for detecting a biomaterial 200 is disclosed. The first fluorescence signal is generated from the first phosphor and the second fluorescence signal is generated from the second phosphor. Here, the first and second phosphors should be present in a state in which they are not quenched by a quencher of each thereof.

Figure 9:
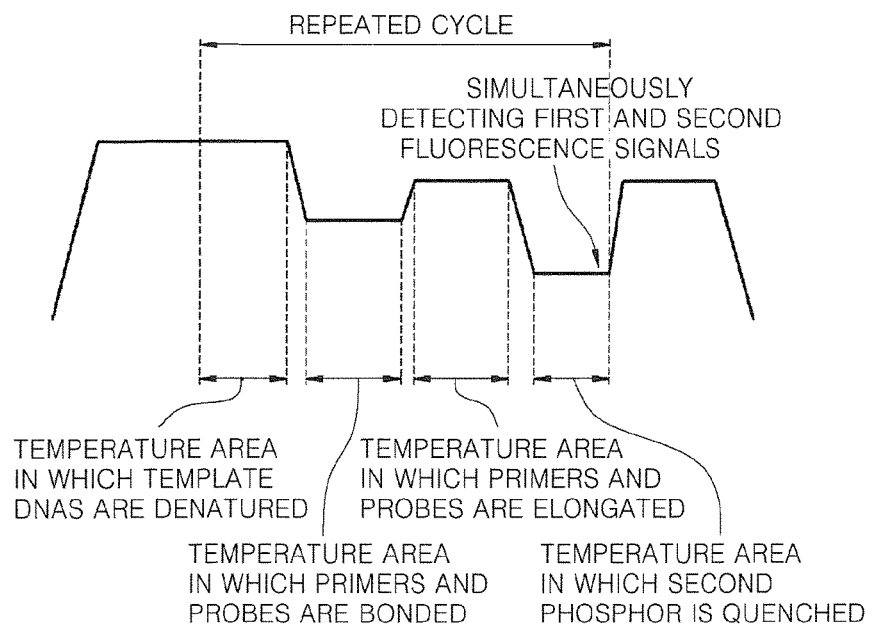
FIGS. 9 and 10 schematically illustrate real-time quantitative and qualitative analyses processes for a biomaterial according to an embodiment of the present invention.

Step (e) is carried out in real-time by means of the fluorometer in a state in which the element part 220 is coupled with the reaction container 210. Preferably, in the detecting (e) after the allowing (d), the secondary structure of the third probe not hybridized with the second probe is recovered, and then, the first and second fluorescence signals are simultaneously detected (see FIG. 9).

Figure 10:
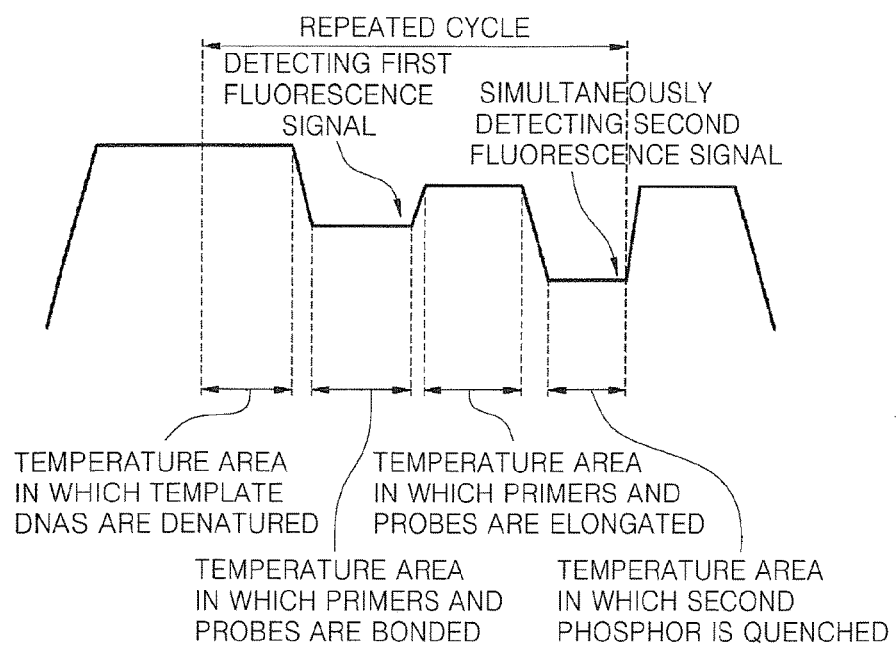

Here, it is preferred to detect the first fluorescence signal while detecting the second fluorescence signal. However, detection of the fluorescence signals may be separately and independently performed so as to increase detection efficiency. That is, when the second probe is hybridized with the third probe and the third probe is present in an elongated state through step (d) and the additional step of quenching the third probe, after first detecting the first fluorescence signal generated by the first phosphor disassembled and released from the complex through real-time PCR of step (c), the second fluorescence signal generated from the second phosphor included in the third probe may be secondarily detected (see FIG. 10).

When target genes having sequences complementary to the first probe are present in the sample, the intensities of the first and second fluorescence signals increase with increasing repetitive cycle number of the reaction. In addition, the first and second fluorescence signals may be detected by means of the fluorometer in a state in which the element part 220 is coupled with the reaction container 210. Preferably, the first and second phosphors generate fluorescence signals detected in different wavelength ranges.

In another embodiment, so as to increase sensitivity of the quantitative and qualitative analysis, at least one of the first and second phosphors may include a plurality of fluorescent materials generating fluorescence signals detected in different wavelength ranges.

For example, the fluorescence signal is provided by obtaining, by means of a camera, images provided from an upper part of the device for detecting a biomaterial 200. As described above, multiples analyses may be carried out by designing various probes, and, since fluorescence signals change in proportion to gene amplification, quantitative and qualitative analyses may be carried out.

Figure 11:
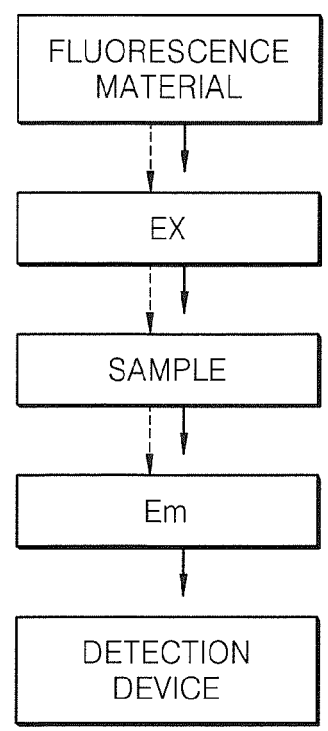
FIGS. 11 to 13 illustrate embodiments of fluorescence signal detection methods.
Figure 12:
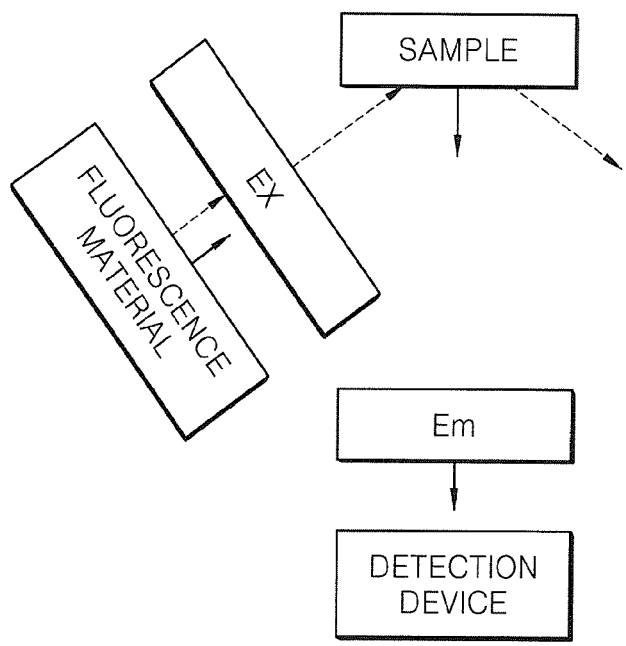
Figure 13:
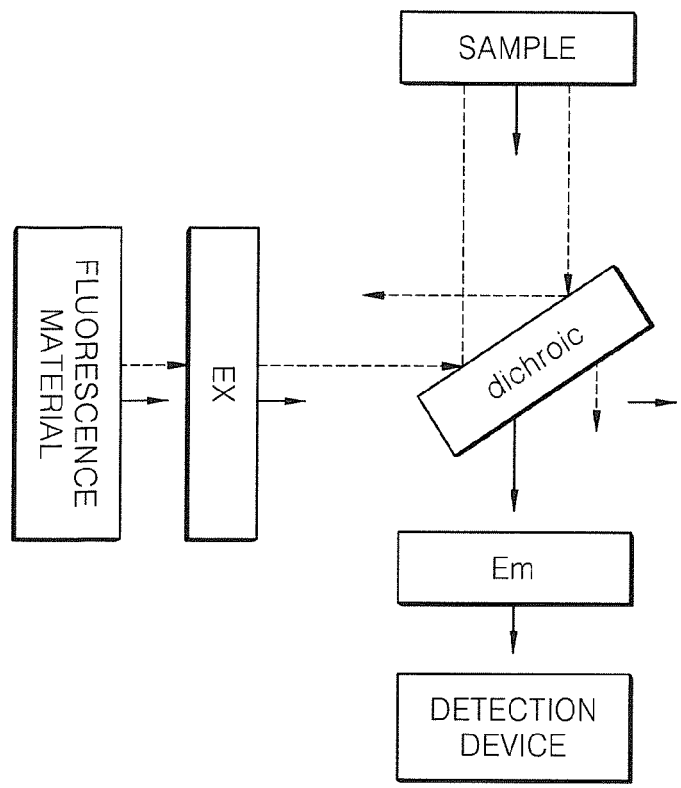

In an embodiment, the first and second fluorescence signals may be detected according to a trans-type fluorescence signal detection method which is carried out in an upper direction of the cap (see FIG. 11). In another embodiment, the first and second fluorescence signals may be detected according to an oblique-type fluorescence signal detection method which is carried out at a constant slope to a surface of the biochip (see FIG. 12). In yet another embodiment, the first and second fluorescence signals may be detected according to an epi-type fluorescence signal detection method which is carried out using a dichroic material in a side direction of the biochip (see FIG. 13).

According to an embodiment of the present invention, the method may be carried out in a thermal cycler to automatically control reaction temperature, reaction time, and frequency of repeated cycles. Here the reaction temperature, the reaction time, and the frequency of the repeated cycles may be automatically controlled by the thermal cycler in a state in which the element part 220 is coupled with the reaction container 210. In addition, the thermal cycler further includes a fluorometer, and thus, real-time quantitative and qualitative analyses for a biomaterial may be carried out in one device.

While the present invention has been described referring to the preferred embodiments of the present invention, those skilled in the art will be able to variously change and modify the present invention through addition, change, or deletion of constituents without departing from the spirit of the present invention, and these modifications will be included within the scope of the present invention.

The invention claimed is:

1. A method of quantitatively and qualitatively analyzing a biomaterial in real-time, the method comprising:
preparing a device for detecting a biomaterial, wherein the device comprises a reaction container comprising an opening at an upper part thereof; and an element part separately connected to the reaction container via the opening, wherein the element part comprises a cap coupled to the opening of the reaction container; and a rod extended from a lower part of the cap, wherein the rod comprises a biochip having a third probe fixed to a surface of the biochip;
feeding a complex of first and second probes, a forward primer, a reverse primer, a sample comprising deoxynucleotide triphosphate (dNTP), a polymerase having exonuclease activity, and a sample comprising target genes, and a reaction solution comprising a buffer into the reaction container, wherein the first probe comprises oligonucleotide sequences complementary to nucleic acid sequences of the target genes in the sample, a first phosphor for generating a first fluorescence signal, and a first quencher for quenching the first phosphor, the second probe does not comprise oligonucleotide sequences complementary to the nucleic acid sequences of the target genes in the sample, but comprises oligonucleotide sequences complementary to the third probe, and the forward and reverse primers comprise oligonucleotide sequences complementary to the nucleic acid sequences of the target genes to amplify the target genes in the sample;

performing polymerase chain reaction comprising denaturation of the target genes in the sample, hybridization of the target genes, the complex, and the forward and reverse primers in the sample, and elongation of the primers through the polymerase having exonuclease activity, wherein the hybridization is only performed between the target genes and the first probe of the complex, and when the polymerase reaches the complex hybridized with the target genes during the elongation by the polymerase having the exonuclease activity, the second probe and the first phosphor are disassembled and released from the complex hybridized with the target genes by the exonuclease activity of the polymerase, and a first fluorescence signal is generated by the first phosphor;

allowing for DNA microarray in which elongation of the second probe on the third probe by the polymerase after hybridizing the released second probe and the third probe fixed to the biochip are performed, wherein the third probe comprises a second phosphor for generating a second fluorescence signal and a second quencher for quenching the second phosphor, and as the second probe is elongated on the third probe, the secondary structure of the third probe is disassembled, and the second quencher is spaced from the second phosphor, and a second fluorescence signal is generated by the second phosphor; and detecting a first fluorescence signal by the first phosphor and a second fluorescence signal by the second phosphor.

2. The method according to claim 1, wherein the feeding comprises adding a reaction solution such that the biochip provided at the rod is submerged in the reaction solution.

3. The method according to claim 2, wherein the biochip may be provided at at least one area selected from an outer peripheral surface and a lower part of the rod, wherein the at least one area comprising the biochip is submerged in the reaction solution.

4. The method according to claim 1, wherein the third probe is fixed to the biochip by a 5' or 3' terminal polymer material of the third probe.

5. The method according to claim 1, wherein, when target genes having sequences complementary to the first probe are not present in the sample, the first phosphor is quenched by the first quencher and the second phosphor is quenched by the second quencher.

6. The method according to claim 1, wherein, when target genes having sequences complementary to the first probe are present in the sample, the first probe of the complex of the first and second probes and the forward and reverse primers are hybridized to complementary sites of the target genes after denaturation of double-stranded template DNAs of the target genes, and the second probe is bonded to the first probe, but is not hybridized with the target genes.

7. The method according to claim 1, wherein, in the performing, the elongation is carried out by a polymerase having 5' exonuclease activity at an elongation temperature of the primers, and during the elongation of the primers, the second probe and the first phosphor are disassembled by the polymerase and released from the complex hybridized at complementary sites of the target genes.

8. The method according to claim 1, wherein the second phosphor and the second quencher comprised in the third probe are disposed closely to each other to exist in a secondary structure in which the second phosphor is quenched by the second quencher.

9. The method according to claim 8, wherein the second phosphor is not quenched by the second quencher at a temperature at which the double-stranded template DNAs of the target genes are denatured.

10. The method according to claim 1, wherein the secondary structure of the third probe maintains an unwound state by elongating the second probe on the third probe with the polymerase after hybridizing the second probe released in the performing with the third probe present in a state in which a secondary structure thereof is unwound.

11. The method according to claim 1, wherein the performing, the allowing, and the detecting are sequentially carried out through repeated cycling in a device for detecting a biomaterial.

12. The method according to claim 1, wherein the performing, the allowing, and the detecting are independently carried out through repeated cycling in the same device for detecting a biomaterial.

13. The method according to claim 11, wherein the second probe disassembled and released from the complex through the performing at a first cycle is hybridized with the third probe fixed to the biochip at a hybridization temperature of the performing at a second cycle.

14. The method according to claim 1, wherein the detecting is carried out in real-time by means of a fluorometer.

15. The method according to claim 14, wherein the detecting is carried out in real time by means of the fluorometer in a state in which the element part is coupled with the reaction container.

16. The method according to claim 1, wherein the method is carried out in a thermal cycler to automatically control reaction temperature, reaction time, and a frequency of repeated cycles.

17. The method according to claim 16, wherein the thermal cycler further comprises a fluorometer.

* * * * *